United States Patent
Daniel et al.

(12)

(10) Patent No.: US 6,184,448 B1
(45) Date of Patent: Feb. 6, 2001

(54) INBRED SUNFLOWER LINE C9607CM

(75) Inventors: Gregory P. Daniel; James R. Lofgren, both of Moorhead, MN (US)

(73) Assignee: Pioneer Hi-Bred International, Inc., Des Moines, IA (US)

( * ) Notice: Under 35 U.S.C. 154(b), the term of this patent shall be extended for 0 days.

(21) Appl. No.: 09/363,297

(22) Filed: Jul. 28, 1999

(51) Int. Cl.$^7$ ................ A01H 5/00; A01H 5/10; A01H 1/04; A01H 4/00; C12N 5/04

(52) U.S. Cl. ............ 800/322; 800/298; 800/260; 800/271; 800/274; 800/278; 435/410; 435/416; 435/428; 435/430

(58) Field of Search ................ 800/322, 298, 800/260, 271, 274, 278; 435/410, 416, 428, 430

*Primary Examiner*—Gary Benzion
*Assistant Examiner*—Melissa L. Kimball

(74) *Attorney, Agent, or Firm*—Pioneer Hi-Bred International, Inc.

(57) ABSTRACT

An inbred sunflower line, designated C9607CM, the plants and seeds of inbred sunflower line C9607CM, methods for producing a sunflower plant either inbred or hybrid, produced by crossing the inbred sunflower line C9607CM with itself or with another sunflower plant, and hybrid sunflower seeds and plants produced by crossing the inbred line C9607CM with another sunflower line or plants and to methods for producing a sunflower plant containing in its genetic material one or more transgenes and to the transgenic sunflower plants produced by that method. This invention also relates to inbred sunflower lines derived from the inbred sunflower line C9607CM, to methods for producing other inbred sunflower lines derived from inbred sunflower line C9607CM, and to the inbred sunflower lines derived by the use of those methods.

26 Claims, No Drawings

INBRED SUNFLOWER LINE C9607CM

FIELD OF THE INVENTION

This invention is in the field of sunflower breeding, specifically relating to an inbred sunflower line designated C9607CM.

BACKGROUND OF THE INVENTION

The goal of plant breeding is to combine in a single variety or hybrid various desirable traits. Major objectives in sunflower breeding include improved seed yield, earlier maturity, shorter plant height, uniformity of plant type, and disease and insect resistance. High oil percentage is important in breeding oilseed types whereas large seed size, a high kernel-to-hull ratio, and uniformity in seed size, shape, and color are important objectives in breeding and selection of non oilseed sunflower. Other characteristics such as improved oil quality, protein percentage and protein quality are also important breeding objectives.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Sunflower (*Helianthus annuus* L.), can be bred by both self-pollination and cross-pollination techniques. The sunflower head (inflorescence) usually is composed of about 1,000 to 2,000 individual disk flowers joined to a common base (receptacle). The flowers around the circumference are ligulate ray flowers with neither stamens nor pistil. The remaining flowers are hermaphroditic and protandrous disk flowers.

Natural pollination of sunflower occurs when flowering starts with the appearance of a tube partly exerted from the sympetalous corolla. The tube is formed by the five syngenesious anthers, and pollen is released on the inner surface of the tube. The style lengthens rapidly and forces the stigma through the tube. The two lobes of the stigma open outward and are receptive to pollen but out of reach of their own pollen initially. Although this largely prevents self-pollination of individual flowers, flowers are exposed to pollen from other flowers on the same head by insects, wind, and gravity.

A reliable method of controlling male fertility in plants offers the opportunity for improved plant breeding. This is especially true for development of sunflower hybrids, which relies upon some sort of male sterility system. Two types of male sterility, genetic and cytoplasmic, have been found in sunflower.

Hybrid sunflower seed is typically produced by a male sterility system incorporating genetic or cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in sunflower plants, since only the female provides cytoplasm to the fertilized seed. CMS plants are fertilized with pollen from another inbred that is not male-sterile. Pollen from the second inbred may or may not contribute genes that make the hybrid plants male-fertile.

Plant breeding methods involving genetic or cytoplasmic male sterility, or induction of male sterility by gibberellic acid, allow for complete hybridization of lines and hence greater precision in estimating combining ability. Various tester parents and tester schemes are being used. A. V. Anaschenko has conducted extensive testing for general combining ability by the top cross method with chemical emasculation of the female parent with gibberellic acid. He has used open pollinated cultivars, hybrids, and inbred lines as testers. A. V. Anaschenko, *The Initial Material for Sunflower Heterosis Breeding*, Proceedings of the 6th International Sunflower Conference, 391–393 (1974). V. Vranceanu used a monogenic male sterile line as a female parent to test for general combining ability and subsequent diallel cross analysis with artificial emasculation to test for specific combining ability. V. Vranceanu, *Advances in Sunflower Breeding in Romania*, Poc. 4th International Sunflower Conference (Memphis, Tenn.), 136–146 (1970). Recent testing by breeders in the United States has included the rapid conversion of lines to cytoplasmic male sterility by using greenhouses and winter nurseries and subsequent hybrid seed production in isolated crossing blocks using open pollinated cultivars, synthetics, composites, or inbred lines as tester.

There are several methods of conferring genetic male sterility available, such as multiple mutant genes at separate locations within the genome that confer male sterility. According to A. I. Gundaev, *Prospects of Selection in Sunflower for Heterosis*, Sb. Rab. Maslichn. Kult., 3:15–21 (1966), genetic male sterility first was reported in the Soviet Union by Kuptsov in 1934. Since then, numerous investigators have reported genetic male sterility in sunflower. Vranceanu indicated isolation of more than thirty sources of male sterility in the Romanian program, most of which were controlled by a single recessive gene. Diallel cross analysis of ten of these lines indicated the presence of five different genes. The studies of E. D. Putt and C. B. Heiser, Jr. were some of the first reported to assess the value of genetic male sterility to produce hybrid seed. They concluded that lines of partial male sterility may have the most immediate value in commercial production of hybrid seed as not only could the partial male sterile lines hybridize well in crossing plots, they could also be increased and easily maintained. E. D. Putt and C. B. Heiser, Jr., *Male Sterility and Partial Male Sterility in Sunflowers*, Crop Science, 6:165–168 (1966).

In order to produce hybrid seed using complete genetic male sterility, the male sterile locus must be maintained in the heterozygous condition in the female parent. This is accomplished by sib pollinations of male sterile plants (ms ms) with heterozygous male fertile plants (Ms ms) within the female parent. The resultant progeny from the male sterile plants will segregate 1:1 for fertile and sterile plants. When such lines are used in hybrid seed production the fertile plants must be removed prior to flowering to obtain 100% hybridization with the male parent line.

Production of hybrid seed by the genetic male sterile system has the advantage that fertile hybrid plants can be produced using any normal male fertile line as the male parent. Although removal of the male fertile plants was facilitated greatly by the discovery of a close linkage between genes for genetic male sterility and anthocyanin pigment in the seedling leaves, the high labor cost required to remove the male fertile, anthocyanin pigmented plants from the female rows of seed production field is a disadvantage of the genetic male sterile system. In addition, the requirement to incorporate and maintain the link characters in the female parent is another disadvantage of the genetic male sterile system. P. Leclercq, *Une sterilite male utilisable pour la production d hybrides simples de tournesol*, Ann. Amelior. Plant 16:135–144 (1966).

The genetic male sterility system has been replaced largely by the cytoplasmic male sterile and fertility restorer system in most current hybrid sunflower breeding programs. The value of genetic male sterility now appears to be primarily an alternate method of hybrid seed production should problems develop with the use of cytoplasmic male sterility such as occurred in maize with susceptibility to southern corn leaf blight. The system also may have value for developing suitable testers for evaluating inbred lines, and subsequent production of hybrid seed for testing.

Around 1960, the first reports of cytoplasmic sterility indicated that most crosses of cytoplasmic male sterile plants with normal male fertile lines produced progeny with variable percentages of sterile plants. Varying degrees of partial sterility were also reported. Through selection and test crossing, lines that produced 92–96% sterile progeny were developed and utilized in experimental production of hybrid seed. A. I. Gundaev, *Prospects of selection in sunflower for heterosis*, Sb. Rab. Maslichn. Kult., 3:15–21 (1966) and A. I. Gundaev, *Basic principles of sunflower selection*, Genetic Principles of Plant Selection, p. 417–465 (1971). Leclercq in France reported the discovery of cytoplasmic male sterility from an interspecific cross involving *H. petiolaris* Nutt. and *H. annuus* L. This source of cytoplasmic male sterility was shown to be very stable. For more information regarding sunflower breeding and genetics, see Gerhardt N. Fick, and Jerry Miller, *The Genetics and Breeding of Sunflower*, Sunflower Science and Technology, pages 441–558 (1997) incorporated herein by reference.

Cytoplasmic male sterile lines are traditionally developed by the backcrossing method in which desirable lines that have undergone inbreeding and selection for several generations are crossed initially to a plant with cytoplasmic male sterility. Thereafter the inbred line to be converted is used as a recurrent parent in the backcrossing procedure. The final progeny will be genetically similar to the recurrent parent except that it will be male sterile.

Fertility restorer lines are developed by transferring a dominant restorer gene to an established inbred line with normal cytoplasm by backcrossing. If this procedure is used, selected plants must be crossed to a cytoplasmic male sterile line after each generation to determine if the fertility restorer genes are present. A more common procedure is self-pollination and selection of male fertile plants from commercial hybrids or planned crosses of parents having restorer genes in male sterile cytoplasm. This procedure does not require test crossing to a male sterile line during selection because the plants will be fully male fertile if the necessary restoring genes are present.

Typically most fertility-restorer lines in use today have restorer genes in male sterile cytoplasm, are resistant to downy mildew and have recessive branching. The later trait extends the period of pollen production and is useful in obtaining simultaneous flowering with female lines in hybrid seed production fields. Restorer lines RHA271, RHA273, and RHA274 were the first such lines to be developed and have been used widely in producing hybrids in breeding programs throughout the world.

Other methods for conferring male sterility are also available and could be used in developing male sterile and fertility restoring sunflowers. For example Albertsen et al., of Pioneer Hi-Bred, U.S. patent application Ser. No. 07/848,433, have developed a system of nuclear male sterility in corn which could also be used in sunflower which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring male sterility in the art of plant breeding and any method can be used, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/000037 published as WO 90/08828)

Development of Sunflower Inbred Lines

The use of male sterile inbreds is but one factor in the production of sunflower hybrids. The development of sunflower hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

There are many important factors to be considered in the art of plant breeding, such as the ability to recognize important morphological and physiological characteristics, the ability to design evaluation techniques for genotypic and phenotypic traits of interest, and the ability to search out and exploit the genes for the desired traits in new or improved combinations. Such methods have also evolved to assist in breeding programs. The use of DNA markers such as restriction fragment length polymorphisms and randomly amplified polymorphic DNA's (RAPDS) are powerful tools of genetic analysis and have been used extensively in a number of species. Linkages of molecular markers with important agronomic traits such as cyst nematode resistance in potato, powdery mildew resistance in barley, insect resistance in long bean have been established. Markers are also correlated with other plant characteristics like flower color, plant height and fertile period response. Sunflower molecular marker technologies are in the early stages of development and isozyme polymorphisms have been used to characterize inbred lines and will be a valuable tool in assisting breeders with selection.

The objective of commercial sunflower hybrid development programs is to develop new inbred lines to produce hybrids that combine to produce high yields and superior agronomic performance. The primary trait breeders seek is yield. However, many other major agronomic traits are of importance in hybrid combination and have an impact on yield or otherwise provide superior performance in hybrid combinations. Major objectives in sunflower breeding include improved seed yield, improved seed oil percentage and oil quality, earlier maturity, shorter plant height, uniformity of plant type, and disease and insect resistance. In addition, the lines per se must have acceptable performance for parental traits such as seed yields and pollen production, all of which affect ability to provide parental lines in sufficient quantity and quality for hybridization. These traits have been shown to be under genetic control and many if not all of the traits are affected by multiple genes.

The trait of primary economic importance in sunflower yield exhibits considerable genetic variability and is often associated with other traits, such as stem fasciation, trichome length, serration of leaf margin, and chlorotic leaf color to name a few. Inbred lines which are used as parents for breeding crosses differ in the number and combination of these genes. These factors make the plant breeder's task more difficult. Compounding this is evidence that no one line contains the favorable allele at all loci, and that different alleles have different economic values depending on the genetic background and field environment in which the hybrid is grown. Fifty years of breeding experience suggests that there are many genes affecting yield and each of these has a relatively small effect on this trait. The effects are small compared to breeders' ability to measure yield differences in evaluation trials. Therefore, the parents of the breeding cross must differ at several of these loci so that the genetic differences in the progeny will be large enough that breeders can develop a line that increases the economic worth of its hybrids over that of hybrids made with other parents.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_3 \rightarrow F_4$; $F_4 \rightarrow F_5$, etc.

A single cross hybrid sunflower variety is the cross of two inbred lines, each of which has a genotype that complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid sunflower variety involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in sunflower, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)×(C×D). A three-way hybrid is produced from three inbred lines. Two inbreds are crossed (A×B) to create an F1 hybrid, which is then crossed to a third inbred (A×B)×C. Much of the hybrid vigor exhibited by $F_1$ hybrids is lost in the next generation ($F_2$). Consequently, seed from hybrid varieties is not used for planting stock.

It has been shown that most traits of economic value in sunflower are under the genetic control of multiple genetic loci, and that there are a large number of unique combinations of these genes present in elite sunflower germplasm. If not, genetic progress using elite inbred lines would no longer be possible. Much progress has been made in the improvement of sunflower. Over the last 50 years Russian breeders were able to increase seed oil content from about 300 grams/kg in the 1930's to over 500 grams/kg among current cultivars. The introduction of adapted and tested hybrids in the USA in the 1970's was estimated to have resulted in yield increases in excess of 25% as well as significant improvements in disease resistance in agronomic type. Extensive genetic variation is available in sunflowers and breeders are optimistic that new lines with superior combining ability, agronomic type, seed quality traits, and/or disease and insect resistance can be developed. Also the wild species of Helianthus offer tremendous resources of genetic diversity for further improvement.

Biotechnology has also received a great deal of attention as a basic technique for improving sunflower. Embryo culture techniques have been developed which have greatly facilitated crossing with wild species. Regeneration of plants from tissue culture is being used to create new sources of genetic variability. Pugalici et al. 1991. "Plant regeneration and genetic variability from tissue cultures of sunflowers", *Plant Breeding,* 106:114–121. Foreign genes from several species including bean, maize, and Brazil nut have been transferred into sunflower using Agrobacterium tumefaciens. The production of double haploids by anther or microspore culture and the genetic mapping of valuable traits or genes using RFLP's are traditional biotechnology procedures that are useful to breeders.

Sunflower is an important and valuable field crop. Thus, a continuing goal of plant breeders is to develop high-yielding sunflower hybrids that are agronomically sound based on stable inbred lines. The reasons for this goal are obvious: to maximize the amount of seed produced with the inputs used and minimize susceptibility of the crop to environmental stresses. To accomplish this goal, the sunflower breeder must select and develop superior inbred parental lines for producing hybrids. This requires identification and selection of genetically unique individuals that occur in a segregating population. The segregating population is the result of a combination of crossover events plus the independent assortment of specific combinations of alleles at many gene loci that results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

In addition to the preceding problem, it is not known how the genotype will react with the environment. This genotype by environment interaction is an important, yet unpredictable, factor in plant breeding. A breeder of ordinary skill in the art cannot predict the genotype, how that genotype will interact with various environments or the resulting phenotypes of the developing lines, except perhaps in a very broad and general fashion. A breeder of ordinary skill in the art would also be unable to recreate the same line twice from the very same original parents as the breeder is unable to direct how the genomes combine or how they will interact with the environmental conditions. This unpredictability results in the expenditure of large amounts of research resources in the development of a superior new sunflower inbred line.

SUMMARY OF THE INVENTION

According to the invention, there is provided a novel inbred sunflower line, designated C9607CM. This invention thus relates to the seeds of inbred sunflower line C9607CM, to the plants of inbred sunflower line C9607CM, and to methods for producing a sunflower plant produced by crossing the inbred line C9607CM with itself or another sunflower line and to methods for producing a sunflower plant containing in its genetic material one or more transgenes and to the transgenic sunflower plants produced by that method. This invention also relates to inbred sunflower lines derived from inbred sunflower line C9607CM, to methods for producing other sunflower lines derived from inbred sunflower line C9607CM and to the inbred sunflower lines derived by use of those methods. This invention further relates to hybrid sunflower seeds and plants produced by crossing the inbred line C9607CM with another sunflower line.

DEFINITIONS

In the description and examples that follow, a number of terms are used herein. In order to provide a clear and consistent understanding of the specification and claims, including the scope to be given such terms, the following definitions are provided. NOTE: ABS is in absolute terms and %MN is percent of the mean for the experiments in which the inbred or hybrid was grown. NOR (normalized) indicates values expressed as standard deviations from the mean. Ten units on the normalized scale represent one standard deviation. A score of 100 on the NOR scale equals the mean of the experiment. A score of 90 equals one standard deviation below the mean and a score of 110 denotes a value one standard deviation above the mean. These designators will follow the descriptors to denote how the values are to be interpreted. Below are the descriptors used in the data tables included herein.

50PFLW—The number of days it takes for 50 percent of the plants to reach the stage of R5.1 R5.1 is when the ray flowers are visible and the first ring of disk flowers has emerged and flowered.

APDSC—A 1–9 visual rating indicating resistance to aphids. Higher scores indicate higher levels of resistance.

BNKSC—A 1 to 9 visual rating indicating the level of neck breakage. The higher the score the less breakage that occurs.

BRTSC—A 1–9 visual rating indicating the amount of brittle snap, early season stalk breakage due to high winds. The higher the score the less breakage that occurs.

BSKSC—A 1 to 9 visual rating indicating the level of stalk breakage. The higher the score the less breakage that occurs.

CLD TST=COLD TEST. The percent of plants that germinate under cold test conditions.

CTRSSC=A 1 to 9 visual rating indicating the degree of seed set obtained within the sunflower head. A 1 equals a head where only the outer 10% of the head sets seed. A 9 equals a head where 90–100% of the head sets seed.

CYTOPLASMIC MALE STERILE (CMS) PLANT OR INBRED LINE. A sunflower line that produces no viable pollen is called male sterile. Male sterility is inherited maternally, i.e. the male sterile plant is used as the female parent in a cross with pollen from another sunflower. CMS lines are produced by crossing a maintainer line with a sunflower plant with the cytoplasmic male sterility trait and then backcrossing to the maintainer line until a male sterile line that is homologous to the maintainer line in all other respects is developed. CMS lines are also referred to as female lines.

DRYRTE=DRYDOWN RATE. This represents the relative rate at which a hybrid will reach acceptable harvest moisture compared to other hybrids. The rate is measured as days required for a hybrid to dry from 40% grain moisture (DYS40M) to 18% grain moisture (DYS18M). A low number of days indicates a hybrid that dries relatively fast while a high number of days indicates a hybrid that dries slowly.

DNYMSC=A 1 to 9 visual rating indicating the resistance to Downy Mildew (*Plasmopara halstedii*). A higher score indicates greater resistance.

DYS18M=The number of days it takes (from planting) grain in plants to reach 18% moisture.

DYS40M=The number of days it takes (from planting) grain in plants to reach 40% moisture.

DYSR9=The number of days it takes for 50 percent of the plants to reach the R9 developmental stage. This is a stage of physiological maturity that is determined when the back of the flowering head has reached a yellowing stage and the outer bracts of the head have started to brown. This normally is a stage when the seed moisture is at about 30–40% moisture.

RFSC=Fertility restoration score using a 1–9 scale. This rating is used for hybrids only and is a measure of the ability of a restorer line to restore the male fertility in hybrid combination with a CMS female line. Higher scores represent a higher level of fertility restoration.

GENASC=General appearance score. A 1–9 rating for overall hybrid appearance. Higher scores indicate better overall appearance.

HARHT=This is the height of the head at harvest, measured in decimeters.

HARMST=This is a measure of seed moisture taken at harvest time. It is recorded in percentage of moisture to seed weight.

HDSSC=Head shape score. Indicates head shape (1=closed "midge" ball, 2=trumpet, 3=clam, 4=concave, 5=cone, 6=reflex, 7=distorted, 8=convex, 9=flat).

HULVSC—Machine hulling score. 1–9 scale. Higher score reflect better hullability (ability of a hulling machine to remove seed hulls from the kernel).

INC/HA=A calculated trait of the value of oil obtained. Yield (QU/HA) multiplied by the percent oil (OIL10P) multiplied by the average cost paid for sunflower, adjusted for premiums paid based on oil percentage of the grain.

MDGSC=Resistance to the sunflower midge, *Contarinia schulzi*, based on head deformation. Rated on a 1–9 scale, 9=no head deformation (fully resistant), 5=moderate head deformation, 1=severe head deformation (fully susceptible).

OIL10P=The percentage of oil content measured from the harvested grain adjusted to a 10% moisture level.

PCTKER=Kernel or nutmeat to hull ratio expressed as a percentage.

PCTO13=Seed size based on the percentage of grain that passes over a "size 13/64 inch (5.2 mm) round hole screen.

PCTO18=Seed size based on the accumulative percentage of grain that is held on a 18/64 inch (7.1 mm) round hole screen.

PCTO20=Seed size based on the accumulative percentage of grain that is held on a 20/64 inch (7.9 mm) round hole screen.

PCTO22=Seed size based on the percentage of grain that is held on a 22/64 inch (8.7 mm) round hole screen.

PRMFL=Predicted relative maturity based on flowering date. Range is 0–99, higher values indicate later flowering.

PRMPHY=Predicted relative maturity based on physiological maturity (DYSR9). Range is 0–99, higher values indicating later physiological maturity.

PHOSC=A 1 to 9 visual rating indicating the resistance to Phompsis stalk rot (*Phompsis helianthii*). A higher score indicates a greater resistance.

PLTHT=This is the height of the head at flowering, measured in decimeters.

PMASC=A 1 to 9 visual rating indicating the resistance to Phoma stalk rot (*Phoma macdonaidii*. The higher score indicates a greater resistance.

QU/HA=Yield in quintals per hectare.

R160=A measure of the percentage of Palmitic acid found in the oil of the seed as measured by a rapid reading from a gas chromatograph.

R180=A measure of the percentage of Stearic acid found in the oil of the seed as measured by a rapid reading from a gas chromatograph.

R181=A measure of the percentage of Oleic acid found in the oil of the seed as measured by a rapid reading from a gas chromatograph.

R182=A measure of the percentage of Linoleic acid found in the oil of the seed as measured by a rapid reading from a gas chromatograph.

RESTORER LINE. A line possessing the gene or genes to restore male fertility or viable pollen to a sunflower hybrid or inbred line and progeny having a maternal cytoplasm that conditions male sterility. This term is also discussed in the literature. See for e.g. Fick, "Breeding and Genetics," in Sunflower Science and Technology 279–338 (J. F. Carter ed. 1978), the contents of which are incorporated herein by reference.

RHZSC=Resistance to Rhizopus head rot. Rating scale from 1–9. Higher scores indicate greater resistance.

RLGSC=A 1 to 9 visual rating indicating the level of root lodging. The higher the score the less root lodging that occurs.

RSTSC=A 1 to 9 visual rating indicating the resistance to Rust (*Puccinia helianthii*). A higher score indicates greater resistance.

SCLHSC=A 1 to 9 visual rating indicating the resistance to Sclerotinia (*Scierotinia scierotiorum*), head infection. A higher score indicates a greater resistance.

SCLRSC=A 1 to 9 visual rating indicating the resistance to Sclerotinia (*Sclerotinia sclerotiorum*), root and basal stalk infection. A higher score indicates a greater resistance.

SDCSC=A visual seed color score (1=white to 9=black).

SDLSC=A visual seed length score (1=short to 9=long).

SDVSC=Seedling vigor score. 1–9 visual rating taken. Higher scores indicate more seedling vigor (early growth).

SEPSC=Resistance to Septoria leaf spot. Rating scale from 1–9. Higher scores indicate greater resistance.

SLFFER=A 1 to 9 visual rating indicating the degree of self fertility found within a self pollinated head. A score of 1 indicates <10% of the seed sets under a bagged self. A score of 9 indicates that 90–100% of the seed sets under a bagged self.

STKGSC=STAY GREEN. Stay green is the measure of plant health near the time of physiological maturity. A high score indicates better late-season plant health.

STMCSC=A 1 to 9 visual rating indicating the degree of stem curvature and head attitude. A 1 indicates a very pendulous neck and head whereas a 9 indicates virtually no neck bend and an erect head attitude.

SUNFLOWER SEED. Botanically referred to as an "achene", comprised of the pericarp and embryo.

TSTWTM=Test weight of seed measured in kilograms per hectoliter.

VERWSC=A 1 to 9 visual rating indicating the resistance to Verticillium wilt (*Verticillium dahliae*). A higher score indicates a greater resistance.

DETAILED DESCRIPTION OF THE INVENTION

Inbred sunflower lines are typically developed for use in the production of hybrid sunflower lines. Inbred sunflower lines need to be highly homogeneous, homozygous and reproducible to be useful as parents of commercial hybrids. There are many analytical methods available to determine the homozygotic and phenotypic stability of these inbred lines.

The oldest and most traditional method of analysis is the observation of phenotypic traits. The data is usually collected in field experiments over the life of the sunflower plants to be examined. Phenotypic characteristics most often observed are for traits associated with plant morphology, flower morphology, insect and disease resistance, maturity, and yield.

In addition to phenotypic observations, the genotype of a plant can also be examined. There are many laboratory-based techniques available for the analysis. comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

Inbred sunflower line C9607CM is an confection type sunflower line which posses genes capable of restoring fertility to hybrids possessing PET 1 cytoplasm. C9607CM has tall plant stature with large seeds. The inbred also demonstrates an average flowering time of 63 days from planting, and an average of 103 days to harvest ripeness. This inbred is further characterized as single headed, but does have a tendency toward environmental basal branching. It also has lots of long cordate leaves and very good general appearance. The inbred generally has long gray seed with broad white margins and occasional fine white lateral striping. Hybrids generated from this inbred are high yielding with strong agronomic traits.

The inbred has shown uniformity and stability within the limits of environmental influence for all the traits as described above and in the Variety Description Information (Table 1) that follows. The inbred has been self-pollinated a sufficient number of generations with careful attention paid to uniformity of plant type to ensure the homozygosity and phenotypic stability necessary to use in commercial production. The line has been increased both by hand and in isolated fields with continued observation for uniformity. No variant traits have been observed or are expected in C9607CM.

Inbred sunflower line C9607CM, being substantially homozygous, can be reproduced by planting seeds of the line, growing the resulting sunflower plants under self-pollinating or sib-pollinating conditions with adequate isolation, and harvesting the resulting seed, using techniques familiar to the agricultural arts.

TABLE 1

VARIETY DESCRIPTION INFORMATION
INBRED = C9607CM

Class: Non Oilseed Type

| | | |
|---|---|---|
| A. | Maturity: | |
| | No. of Days to Head First Visible(from emergence): | 63 |
| | No. of Days to Harvest Ripeness | 103 |
| | No. of Days to Physiological Maturity: | 119 |
| B. | Plant Characteristics: | |
| | Plant Height (cm): | 152 |
| C. | Stem: | |
| | Length of Internode at Harvest Ripeness (cm) | 4.8 |
| | Number of Leaves (average): | 32 |
| | Branching: | occasional environmental basal branching |
| | Color of Growing Point: | green |
| D. | Leaves: | |
| | Petiole Length (cm): | 12 |
| | Blade Length (cm): | 28 |
| | Blade Width (cm): | 24 |
| | Width: Length Ratio: | narrower than long |
| | Leaf Shape: | cordate |
| | Leaf Apex: | acuminate |
| | Leaf Base: | auriculate |
| | Leaf Margin: | coarsely crenate |
| | Depth of Margin Indentation: | intermediate |
| | Attitude: | ascending |
| | Surface: | crinkled (ridged) |
| | Leaf Color | green |
| | Leaf Margin Color: | green |
| E. | Head at Flowering: | |
| | Young Bud (at 3 cm dia.): | closed |
| | Flowering Ht. Avg. (cm): | 15.6 |
| | Ray Flower: | present |
| | Ray Flower Color: | orange yellow |
| | Disk Flower Color: | yellow |
| | Anthocyanin in Stigma: | absent |
| | Bract Length Avg. (mm): | 56 |
| | Pollen Color: | yellow |
| | Pappi: | green |
| | Ray Flower Attitude | upright |
| | Ray Flower Length (mm): | 60 |
| | Ray Width (mm): | 20 |
| F. | Head at Seed Maturity: | |
| | Head Diameter (cm): | 18 |
| | Receptacle Shape: | flat |
| | Head Attitude: | descending |
| | No. of Seeds Per Head: | 525 |
| G. | Seeds: | |
| | Outer Pericarp: | gray |
| | Middle Pericarp: | white |
| | Inner Pericarp: | no color |
| | Stripes: | broad white margins with occasional fine white lateral stripes |
| | Mottling: | absent |
| | Shape: | narrowly obovate |
| | Shape (Cross Section): | curved |
| | Length (mm): | 15 |
| | Width (mm): | 7 |
| | Gram/100 seed: | 12.4 |
| | % Held on 7.9 mm (20/64) Round-Hole Screen: | 14.7 |

*In interpreting the foregoing color designations, reference may be had to the Munsell Glossy Book of Color, a standard color reference.
All data collected from plots in Woodland, California.

Further Embodiments of the Invention

This invention also is directed to methods for producing a sunflower plant by crossing a first parent sunflower plant with a second parent sunflower plant wherein either the first or second parent sunflower plant is an inbred sunflower plant of the line C9607CM. Further both first and second parent sunflower plants can come from the inbred sunflower plant line C9607CM. Still further this invention also is directed to methods for producing an inbred sunflower line C9607CM-derived sunflower plant by crossing inbred sunflower line C9607CM with a second sunflower plant and growing the progeny seed, and repeating the crossing and growing steps with the inbred sunflower line C9607CM-derived plant from 0 to 5 times. Thus, any such methods using the inbred sunflower line C9607CM are part of the invention; selfing, backcrosses, hybrid production, crosses to populations, and the like. All plants produced using inbred sunflower line C9607CM as a parent are within the scope of this invention, including plants derived from inbred sunflower line C9607CM. Advantageously the inbred sunflower line is used in crosses with other, different sunflower inbreds to produce first generation (F1) sunflower hybrid seeds in plants with superior characteristics.

It should be understood that the inbred can, through routine manipulation of cytoplasmic or other factors, be produced in the male sterile form. Such embodiments are also contemplated within the scope of the present claims. The foregoing was set forth by way of example and is not intended to limit the scope of this invention.

As used herein the term plant includes plant cells, plant protoplast, plant cell tissue cultures from which sunflower plants can be regenerated, plant calli, plant clumps and plant cells that are intact in plants, or parts of plants, such as embryos, pollen, ovules, leaves, stems, cortex, pith, involucral bracts, ray flowers, disk flowers, pappi, achenes, nectaries, interfloral bracts, receptacle, trichomes, stigma, anther, style, filament, calyx, pericarp, seed coat, endosperm, embryo, roots, root tips, seeds and the like.

The first reference of plant regeneration from sunflower callus was by Sadhu 1974. "Affective different auxin on growth and differentiation in callus tissue from sunflower stem pith". M.D. & J. Exp. Biol. 12:110–11 (1974). Sadhu isolated stem pithum and eventually regenerated plantlets from a single piece of callus. Standard tissue culture variables such as methods of staging and preparation of explants, composition of culture media, cultural conditions, timing of the regeneration process, plant establishment, and maintenance of fertility have all been delineated for sunflower. Explant sources have included seedling hypocotyl, mature cotyledon, immature cotyledon, immature embryo-somatic embryogenesis, immature embryo-rescued, primary leaflets, meristem, embryonic axis, half apex, unfertilized ovary or ovule, anther, shoot-tip protoplasts, hypocotyl protoplasts, hypocotyl and cotyledon protoplasts. The most favored explants for culture initiation and plant regeneration are mature cotyledons, immature embryos, hypocotyls and excised meristems. For detailed description of culture systems for *Helianthus annuus* please see Chapter 11, Sunflower Biotechnology, Bidney, D. L. and Scelonge, C. J., pp. 559–593 and references cited therein. Sunflower Technology and Production, edited by A. A. Schneiter, Agronomy 35, publishers, American Society of Agronomy Inc. 1997.

Transformation of Sunflower

With the advent of molecular biological techniques that have allowed the isolation and characterization of genes that encode specific protein products, scientists in the field of plant biology developed a strong interest in engineering the genome of plants to contain and express foreign genes, or additional, or modified versions of native or endogenous genes (perhaps driven by different promoters) in order to alter the traits of a plant in a specific manner. Such foreign, additional and/or modified genes are referred to herein collectively as "transgenes". Over the last fifteen to twenty years several methods for producing transgenic plants have been developed, and the present invention, in particular embodiments, also relates to transgenic versions of the claimed inbred sunflower line C9607CM.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used, alone or in combination with other plasmids, to provide transformed sunflower plants, using transformation methods as described below to incorporate transgenes into the genetic material of the sunflower plant(s).

Expression Vectors For Sunflower Transformation

Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.,* 80: 4803 (1983). Another commonly used selectable marker gene is the hybrimycin phosphotransferase gene which confers resistance to the antibiotic hybrimycin. Vander Ellison et al., *Plant Mol. Boil.,* 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayward et al., *Plant Physiol.* 86: 1216 (1988), Jones et al., *Mol. Gen. Genet.,* 210: 86 (1987), Svab et al., *Plant Mol. Biol.* 14: 197 (1990), Hille et al., *Plant Mol. Biol.* 7: 171 (1986). Other selectable marker genes confer resistance to herbicides such as glyphosate, glufosinate or broxynil. Comai et al., *Nature* 317: 741–744 (1985), Gordon-Kamm et al., *Plant Cell* 2: 603–618 (1990) and Stalker et al., *Science* 242: 419–423 (1988).

Other selectable marker genes for plant transformation are not of bacterial origin. These genes include, for example, mouse dihydrofolate reductase, plant 5-eno/pyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., *Plant Cell Rep.* 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5: 387 (1987)., Teeri et al., *EMBO J.* 8: 343 (1989), Koncz et al., *Proc. Natl. Acad. Sci. U.S.A.* 84:131 (1987), De Block et al., *EMBO J.* 3: 1681 (1984). Another approach to the identification of relatively rare transformation events has been use of a gene that encodes a dominant constitutive regulator of the *Zea mays* anthocyanin pigmentation pathway. Ludwig et al., *Science* 247: 449 (1990).

Recently, in vivo methods for visualizing GUS activity that do not require destruction of plant tissue have been made available. Molecular Probes Publication 2908, Imagene Green™, p. 1–4 (1993) and Naleway et al., *J. Cell Biol.*115: 15Ia (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in sunflower. Optionally, the inducible promoter is operably linked to a nucleotide sequence encoding a signal sequence which is operably linked to a gene for expression in sunflower. With an inducible promoter the rate of transcription increases in response to an inducing agent.

Any inducible promoter can be used in the instant invention. See Ward et al. *Plant Mol. Biol.*22: 361–366 (1993). Exemplary inducible promoters include, but are not limited to, that from the ACEI system which responds to copper (Mett et al. *PNAS* 90: 4567–4571 (1993)); In2 gene from sunflower which responds to benzenesulfonamide herbicide safeners (Hershey et al., *Mol. Gen. Genetics* 227: 229–237 (1991) and Gatz et al., *Mol. Gen. Genetics* 243: 32–38 (1994)) or Tet repressor from Tn20 (Gatz et al., *Mol. Gen. Genet.* 227: 229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88: 0421 (1991).

B. Constitutive Promoters

A constitutive promoter is operably linked to a gene for expression in sunflower or the constitutive promoter is operably linked to a nucleotide sequence encoding a signal sequence which is operably linked to a gene for expression in sunflower.

Many different constitutive promoters can be utilized in the instant invention. Exemplary constitutive promoters include, but are not limited to, the promoters from plant viruses such as the 35S promoter from CaMV (Odell et al., *Nature* 313: 810–812 (1985) and the promoters from such genes as rice actin (McElroy et al., *Plant Cell* 2: 163–171 (1990)); ubiquitin (Christensen et al., *Plant Mol. Biol* 12: 619–632 (1989) and Christensen et al., *Plant Mol. Biol.* 18: 675–689 (1992)): pEMU (Last et al., *Theor. Appl. Genet.* 81: 581–588 (1991)); MAS (Velten et al., *EMBO J.* 3: 2723–2730 (1984)) and maize H3 histone (Lepetit et al., *Mol. Gen. Genet.* 231: 276–285 (1992) and Atanassova et al., *Plant Journal* 2 (3): 291–300 (1992)).

The ALS promoter, a Xbal/Ncol fragment 5' to the *Brassica napus* ALS3 structural gene (or a nucleotide sequence that has substantial sequence similarity to said Xbal/Ncol fragment), represents a particularly useful constitutive promoter. See PCT application WO96/30530.

C. Tissue-specific or Tissue-Preferred Promoters

A tissue-specific promoter is operably linked to a gene for expression in sunflower. Optionally, the tissue-specific promoter is operably linked to a nucleotide sequence encoding a signal sequence which is operably linked to a gene for expression in sunflower. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23: 476–482 (1983) and Sengupta-Gopalan et al., *Proc. Natl. Acad. Sci. USA* 82: 3320–3324 (1985)); a leaf-specific and light-induced promoter such as that from cab or rubisco (Simpson et al., *EMBO J.* 4(11): 2723–2729 (1985) and Timko et al., *Nature* 318: 579–582 (1985)); an anther-specific promoter such as that from LAT52 (Twell et al., *Mol. Gen. Genet.* 217: 240–245 (1989)); a pollen-specific promoter such as that from Zm13 (Guerrero et al., *Mol. Gen. Genet.*224: 161–168 (1993)) or a microspore-preferred promoter such as that from apg (Twell et al., *Sex. Plant Reprod.* 6: 217–224 (1993).

Signal Sequences For Targeting Proteins to Subcellular Compartments

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art. See, for example, Becker et al., *Plant Mol. Biol.*20: 49 (1992), Close, P. S., Master's Thesis, Iowa State University (1993), Knox, C., et al., "Structure and Organization of Two Divergent Alpha-Amylase Genes From Barley", *Plant Mol.Biol.* 9: 3–17 (1987), Lerner et at., *Plant Physiol.*91: 124–129 (1989), Fontes et al., *Plant Cell* 3: 483–496 (1991), Matsuoka et al., *Proc. Natl. Acad. Sci.* 88: 834 (1991), Gould et al., *J. Cell Biol* 108: 1657 (1989), Creissen et al., *Plant J.* 2: 129 (1991), Kalderon, D., Robers, B., Richardson, W., and Smith A., "A short amino acid sequence able to specify nuclear location", *Cell* 39: 499–509 (1984), Stiefel, V., Ruiz-Avila, L., Raz R., Valles M., Gomez J., Pages M., Martinez-Izquierdo J., Ludevid M., Landale J., Nelson T., and Puigdomenech P., "Expression of a maize cell wall hydroxyproline-rich glycoprotein gene in early leaf and root vascular differentiation", *Plant Cell* 2: 785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92–6 (1981).

According to a preferred embodiment, the transgenic plant provided for commercial production of foreign protein is sunflower. In another preferred embodiment, the biomass of interest is seed. For the relatively small number of transgenic plants that show higher levels of expression, a genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, Boca Raton,1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below.

1. Genes That Confer Resistance To Pests or Disease And That Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (Arabidopsis RSP2 gene for resistance to *Pseudomonas syringae*).

(B) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt δ-endotoxin gene. Moreover, DNA molecules encoding δ-endotoxin genes can be purchased from American Type Culture Collection (Rockville, Md.), for example, under ATCC Accession Nos. 40098, 67136, 31995 and 31998.

(C) A lectin. See, for example, the disclosure by Van Damme et al., *Plant Molec. Biol.* 24: 25 (1994), who disclose the nucleotide sequences of several *Clivia miniata* mannose-binding lectin genes.

(D) A vitamin-binding protein, such as avidin. See PCT application US93/06487 the contents of which are hereby incorporated by. The application teaches the use of avidin and avidin homologues as larvicides against insect pests.

(E) An enzyme inhibitor, for example, a protease inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor I), and Sumitani et al., *Biosci. Biotech. Biochem.* 57: 1243 (1993) (nucleotide sequence of *Streptomyces nitrosporeus* α-amylase inhibitor).

(F) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

(H) An insect-specific venom produced in nature by a snake, a wasp, etc. For example, see Pang et al., Gene 116: 165 (1992), for disclosure of heterologous expression in plants of a gene coding for a scorpion insectotoxic peptide.

(I) An enzyme responsible for an hyperaccumulation of a monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

(K) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(L) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

(M) A membrane permease, a channel former or a channel blocker. For example, see the disclosure by Jaynes et al., *Plant Sci.* 89: 43 (1993), of heterologous expression of a cecropin-β lytic peptide analog to render transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(O) An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland, 1994) (enzymatic inactivation in transgenic tobacco via production of single-chain antibody fragments).

(P) A virus-specific antibody. See, for example, Tavladoraki et al., Nature 366: 469 (1993), who show that transgenic plants expressing recombinant antibody genes are protected from virus attack.

(Q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(R) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

2. Genes That Confer Resistance To A Herbicide, For Example:

(A) A herbicide that inhibits the growing point or meristem, such as an imidazalinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+genes) and a benzonitrile (nitrilase gene). Przibilla et al., *Plant Cell* 3: 169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

3. Genes That Confer Or Contribute To A Value-Added Trait, Such As:

(A) Modified fatty acid metabolism, for example, by transforming a plant with an antisense gene of stearoyl-ACP desaturase to increase stearic acid content of the plant. See Knultzon et al., *Proc. Natl. Acad. Sci. USA* 89: 2624 (1992).

(B) Decreased phytate content
  (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.
  (2) A gene could be introduced that reduces phytate content. In maize, this, for example, could be accomplished, by cloning and then reintroducing DNA associated with the single allele which is responsible for maize mutants characterized by low levels of phytic acid. See Raboy et al., *Maydica* 35: 383 (1990).

(C) Modified carbohydrate composition effected, for example, by transforming plants with a gene coding for an enzyme that alters the branching pattern of starch. See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* α-amylase), Elliot et al., *Plant Molec. Biol.* 21: 515 (1993) (nucleotide sequences of tomato invertase genes), Søgaard et al., *J. Biol. Chem.* 268: 22480 (1993) (site-directed mutagenesis of barley α-amylase gene), and Fisher et al., *Plant Physiol.* 102: 1045 (1993) (maize endosperm starch branching enzyme 11).

Methods for Sunflower Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89–119.

A. Agrobacterium-mediated Transformation

One method for introducing an expression vector into plants is based on the natural transformation system of Agrobacterium. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.*10: 1 (1991). Descriptions of Agrobacterium vector systems and methods for Agrobacterium-mediated gene transfer are provided by Gruber et al., supra, Miki et al., supra, and Moloney et al., *Plant Cell Reports* 8: 238 (1989). See also, U.S. Pat. No. 5,591,616, issued Jan. 7, 1997. The first sunflower transformations with engineered strains of Agrobacterium were reported in 1983 in which Phaseolin was inserted into T-DNA of the Ti plasmid and inoculated to sunflower seedlings. Murai et al. (1983) "Phaseolin Gene From Bran is Expressed After Transfer to Sunflower", *Science,* 222:475482. Sunflower is susceptible to Agrobacterium infection and it remains the most efficient and popular transformation protocol. Knittel et al., "Transformation of Sunflower/*Helianthus annuus* L.) A Retrievable Protocol", *Plant Cell Rep.* 14:81–86; Malone-Schoneberg, J., et al. 1994, "Stable Transformation of Sunflower Using Agrobacterium and Split Embryonic Axis Explants", *Plant Science,* 103:119–207.

B. Direct Gene Transfer

Despite the fact the host range for Agrobacterium-mediated transformation is broad, some major cereal crop species and gymnosperms have generally been recalcitrant to this mode of gene transfer, even though some success has recently been achieved in rice and maize. Hiei et al., *The Plant Journal* 6: 271–282 (1994); U.S. Pat. No. 5,591,616, issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559–563 (1988), Sanford, J. C., *Physiol Plant* 79: 206 (1990), Klein et al., *Biotechnology* 10: 268 (1992). Several target tissues can be bombarded with DNA-coated microprojectiles in order to produce transgenic plants, including, for example, callus (Type I or Type II), immature embryos, and meristematic tissue. In sunflower microprojectile bombardment efficiency is low. Experiments with sunflower meristems designed to compare stable transformation efficiency of microprojectile bombardment to deliver plasmid DNA with bombardment used only to induce wounds to facilitate Agrobacterium transformation showed the frequency of positive transformants nearly 300 fold higher in the latter protocol. Bidney et al., "Microprojectile Bombardment of Plant Tissues Increases Transformation Frequency by *Agrobacterium tumefaciens*", *Plant Mol. Biol.* 18:301–313 (1993).

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.*, 4: 2731 (1985), Christou et al., *Proc Natl. Acad. Sci. U.S.A.* 84: 3962 (1987). Direct uptake of DNA into protoplasts using CaCl2 precipitation, polyvinyl alcohol or poly-L-ornithine have also been reported. Hain et al., *Mol. Gen. Genet.*199: 161 (1985) and Draper et al., *Plant Cell Physiol.*23: 451 (1982). Electroporation of protoplasts and whole cells and tissues have also been described. Donn et al., In Abstracts of VIIth International Congress on Plant Cell and Tissue Culture IAPTC, A2–38, p 53 (1990); D'Halluin et al., *Plant Cell* 4: 1495–1505 (1992) and Spencer et al., *Plant Mol. Biol.* 24: 51–61 (1994).

Following transformation of sunflower target tissues, expression of the above-described selectable marker genes allows for preferential selection of transformed cells, tissues and/or plants, using regeneration and selection methods now well known in the art.

Several sunflower transformant protocols have evolved which allow for the identification of transformants without the need for selectable markers. Nutler et al. 1987, "Factors Affecting the Level of Kanamycin Resistance in Transformed Sunflower Cells", *Plant Physiol.* 84:1185–1192. See also, Bidney, D., et al., supra, using intact meristem explants and analyzing gene in leaf tissue via protein methods such as ELISA or enzyme assay or nucleic acid methods such as PCR or RT-PCTR.

The foregoing methods for transformation would typically be used for producing transgenic inbred lines. Transgenic inbred lines could then be crossed, with another (non-transformed or transformed) inbred line, in order to produce a transgenic hybrid sunflower plant. Alternatively, a genetic trait which has been engineered into a particular sunflower line using the foregoing transformation techniques could be moved into another line using traditional backcrossing techniques that are well known in the plant breeding arts. For example, a backcrossing approach could be used to move an engineered trait from a public, non-elite line into an elite line, or from a hybrid sunflower plant containing a foreign gene in its genome into a line or lines which do not contain that gene. As used herein, "crossing" can refer to a simple X by Y cross, or the process of backcrossing, depending on the context.

INDUSTRIAL APPLICABILITY

Sunflower (*Helianthus annuus*) oil is a major edible oil worldwide. The oil component of sunflower seeds typically contributes about 80 percent of the value of a sunflower crop and is mostly used as a cooking medium. Sunflower oil is also used as salad oil, as well as in the manufacture of margarine, soap, shortening, lubricants, and as a source for biodiesel fuels. In the United States, approximately 1–2 million acres are planted in sunflowers annually, primarily in the Dakotas and Minnesota.

The seed of inbred sunflower line C9607CM, the plant produced from the inbred seed, the hybrid sunflower plant produced from the crossing of the inbred, hybrid seed, and various parts of the hybrid sunflower plant can be utilized for human food, livestock feed, and as a raw material in industry.

Performance Examples of C9607CM

In the examples that follow, the traits and characteristics of inbred sunflower line C9607CM are given as a line. The data collected on inbred sunflower line C9607CM is presented for the key characteristics and traits.

Table 2A is a paired hybrid comparison report which compares inbred Sunflower line C9607CM and Pioneer Hi-Bred proprietary Sunflower line C9604CM in hybrid combination with Pioneer Hi-Bred proprietary sunflower line D116A. As can be seen from the results, the C9607CM hybrids are significantly earlier flowering than the C9604CM hybrids. The C9607CM hybrids are also above average in resistance to the sunflower midge, *Contarinia schulzi*, in general overall appearance, and in yield. C9607CM hybrids further exhibit significantly taller plant stature than C9604CM hybrids.

Table 2B is a paired comparison report which compares Inbred Pioneer Hi-Bred Sunflower line C9607CM and Pioneer Hi-Bred proprietary inbred C9606CM in hybrid combination with Pioneer Hi-Bred proprietary sunflower line Dl 16A. As can be seen from the results the C9607CM hybrids demonstrate significantly superior resistance to the sunflower midge, *Contarinia schulzi* than the C9606CM hybrids. The C9607CM hybrids further exhibit a significantly larger seed size (PCT 020 and PCT 018) than the C9606CM hybrids. The C9607CM hybrids further demonstrate above average plant height, yield, and general appearance.

Table 2C is a paired comparison report which compares Inbred Pioneer Hi-Bred Sunflower line C9607CM and Pioneer Hi-Bred proprietary inbred C9634CM in hybrid combination with Pioneer Hi-Bred proprietary sunflower line D116A. As can be seen from the results the C9607CM hybrids demonstrate significantly taller plant stature than the C9634CM hybrids. The C9607CM hybrids further exhibit above average yield, general appearance, and resistance to the sunflower midge, *Contarinia schulzi*.

TABLE 2A

PAIRED COMPARISON REPORT
VARIETY #1 - D116A/C9607CM
VARIETY#2 - D116A/C9604CM

|  | VAR # | QU/ HA ABS | QU HA % MN | HAR MST ABS | 50P FLW ABS | DYS R9 ABS | DYS R9 % MN | PRM PHY |
|---|---|---|---|---|---|---|---|---|
| TOTAL SUM | 1 | 17.8 | 118 | 14.0 | 66.7 | 116.5 | 100 | .37 |
|  | 2 | 16.4 | 112 | 15.4 | 67.7 | 116.7 | 100 | .37 |
|  | LOCS | 6 | 6 | 6 | 3 | 3 | 3 | 2 |
|  | REPS | 12 | 12 | 12 | 6 | 6 | 6 | 2 |
|  | DIFF | 1.3 | 7 | 1.4 | 1.0 | 0.2 | 0 | 1 |
|  | PROB | .266 | .428 | .175 | .000# | .899 | .932 | .715 |

|  | VAR # | PLT HT ABS | PLT HT % MN | BSK SC % MN | RLG SC % MN | GEN ASC % MN | RF SC ABS | PHO SC NOR |
|---|---|---|---|---|---|---|---|---|
| TOTAL SUM | 1 | 18.3 | 111 | 100 | 93 | 115 | 9.0 | 75 |
|  | 2 | 15.3 | 92 | 96 | 109 | 127 | 3.0 | 90 |
|  | LOCS | 3 | 3 | 2 | 1 | 6 | 2 | 1 |
|  | REPS | 3 | 3 | 4 | 2 | 12 | 4 | 2 |
|  | DIFF | 3.0 | 19 | 4 | 16 | 13 | 6.0 | 15 |
|  | PROB | .035+ | .056* | .874 |  | .276 | .205 |  |

|  | VAR # | MDG SC NOR | PCT 022 ABS | PCT 020 ABS | PCT 018 ABS | PCT KER ABS | SDL SC ABS | SDC SC ABS |
|---|---|---|---|---|---|---|---|---|
| TOTAL SUM | 1 | 109 | 10.9 | 54.3 | 84.7 | 58.5 | 7.0 | 7.8 |
|  | 2 | 111 | 21.0 | 59.9 | 86.1 | 58.2 | 7.8 | 8.0 |
|  | LOCS | 2 | 5 | 5 | 5 | 3 | 2 | 2 |
|  | REPS | 4 | 9 | 9 | 9 | 5 | 4 | 4 |
|  | DIFF | 2 | 10.2 | 5.6 | 1.4 | 0.3 | 0.8 | 0.3 |
|  | PROB | .859 | .253 | .361 | .338 | .662 | .205 | .500 |

|  | VAR # | HD SSC ABS |
|---|---|---|
| TOTAL SUM | 1 | 7.3 |
|  | 2 | 9.0 |
|  | LOCS | 3 |
|  | REPS | 3 |
|  | DIFF | 1.7 |
|  | PROB | .423 |

10% SIG
+ = 5% SIG
# = 1% SIG

TABLE 2B

PAIRED COMPARISON REPORT
VARIETY#1 - D116A/C9607CM
VARIETY #2 - D116A/C9606CM

|  | VAR # | QU/ HA ABS | QU HA % MN | HAR MST ABS | 50P FLW ABS | DYS R9 ABS | DYS R9 % MN | PRM PHY |
|---|---|---|---|---|---|---|---|---|
| TOTAL SUM | 1 | 22.4 | 119 | 13.5 | 66.7 | 116.6 | 100 | 37 |
|  | 2 | 22.4 | 120 | 12.7 | 64.8 | 116.2 | 99 | 37 |
|  | LOCS | 9 | 9 | 9 | 3 | 5 | 5 | 2 |
|  | REPS | 17 | 17 | 17 | 6 | 10 | 10 | 2 |
|  | DIFF | 0.0 | 0 | 0.8 | 1.8 | 0.4 | 0 | 1 |
|  | PROB | .999 | .962 | .142 | .093* | .596 | .568 | .548 |

|  | VAR # | PLT HT ABS | PLT HT % MN | BSK SC % MN | RLG SC % MN | GEN ASC % MN | RF SC ABS | PHO SC NOR |
|---|---|---|---|---|---|---|---|---|
| TOTAL SUM | 1 | 18.3 | 112 | 100 | 93 | 114 | 9.0 | 78 |
|  | 2 | 17.5 | 107 | 109 | 101 | 123 | 9.0 | 84 |
|  | LOCS | 4 | 4 | 2 | 1 | 9 | 2 | 2 |
|  | REPS | 4 | 4 | 4 | 2 | 18 | 4 | 4 |

TABLE 2B-continued

PAIRED COMPARISON REPORT
VARIETY#1 - D116A/C9607CM
VARIETY #2 - D116A/C9606CM

|  |  |  |  |  |  |  |  |  |
|---|---|---|---|---|---|---|---|---|
|  | DIFF | 0.8 | 4 | 8 | 8 | 9 | 0.0 | 6 |
|  | PROB | .215 | .213 | .500 |  | .132 | 1.00 | .500 |

| | VAR # | MDG SC NOR | PCT 022 ABS | PCT 020 ABS | PCT 018 ABS | PCT KER ABS | SDL SC ABS | SDC SC ABS |
|---|---|---|---|---|---|---|---|---|
| TOTAL SUM | 1 | 109 | 11.7 | 52.1 | 83.2 | 58.5 | 7.2 | 7.5 |
| | 2 | 91 | 6.4 | 37.2 | 78.0 | 54.1 | 7.0 | 7.7 |
| | LOCS | 2 | 7 | 7 | 7 | 3 | 3 | 3 |
| | REPS | 4 | 13 | 13 | 13 | 5 | 6 | 6 |
| | DIFF | 18 | 5.3 | 14.9 | 5.2 | 4.4 | 0.2 | 0.2 |
| | PROB | .017+ | .060* | .002# | .028+ | .206 | .423 | .423 |

| | VAR # | HD SSC ABS | SCL RSC NOR |
|---|---|---|---|
| TOTAL SUM | 1 | 7.3 | 100 |
| | 2 | 7.0 | 89 |
| | LOCS | 3 | 1 |
| | REPS | 3 | 2 |
| | DIFF | 0.3 | 11 |
| | PROB | .423 |  |

* = 10% SIG
+ = 5% SIG
# = 1% SIG

TABLE 2C

PAIRED COMPARISON REPORT
VARIETY#1 - D116A/C9607CM
VARIETY #2 - D116A/C9634CM

| | VAR # | QU/ HA ABS | QU HA % MN | HAR MST ABS | 50P FLW ABS | DYS R9 ABS | DYS R9 % MN | PRM PHY |
|---|---|---|---|---|---|---|---|---|
| TOTAL SUM | 1 | 29.8 | 128 | 12.2 | 69.0 | 117.0 | 99 | 36 |
| | 2 | 22.4 | 108 | 14.5 | 70.5 | 121.3 | 103 | 39 |
| | LOCS | 4 | 4 | 4 | 1 | 3 | 3 | 1 |
| | REPS | 7 | 7 | 7 | 2 | 6 | 6 | 1 |
| | DIFF | 7.5 | 19 | 2.3 | 1.5 | 4.3 | 4 | 2 |
| | PROB | .417 | .44 | .189 |  | .281 | .272 |  |

| | VAR # | PLT HT ABS | PLT HT % MN | BSK SC % MN | RLG SC % MN | GEN ASC % MN | RF SC ABS | PHO SC NOR |
|---|---|---|---|---|---|---|---|---|
| TOTAL SUM | 1 | 17.5 | 114 | 122 | 81 | 119 | 12.5 | 49.9 |
| | 2 | 14.5 | 95 | 87 | 111 | 113 | 7.1 | 18.2 |
| | LOCS | 2 | 2 | 4 | 1 | 1 | 3 | 3 |
| | REPS | 2 | 2 | 7 | 2 | 2 | 5 | 5 |
| | DIFF | 3.0 | 20 | 35 | 30 | 6 | 5.4 | 31.6 |
| | PROB | .000# | .023+ | .052* |  |  | .125 | .105 |

| | VAR # | MDG SC NOR | PCT 022 ABS | PCT 020 ABS | PCT 018 ABS | PCT KER ABS | SDL SC ABS | SDC SC ABS |
|---|---|---|---|---|---|---|---|---|
| TOTAL SUM | 1 | 81.0 | 65.6 | 7.5 | 7.0 | 4.0 | 100 |  |
| | 2 | 43.8 | 50.2 | 6.0 | 6.5 | 8.0 | 94 |  |
| | LOCS | 3 | 1 | 1 | 1 | 1 | 1 |  |
| | REPS | 5 | 1 | 2 | 2 | 1 | 2 |  |
| | DIFF | 37.1 | 15.3 | 1.5 | 0.5 | 4.0 | 6 |  |
| | PROB | .097* |  |  |  |  |  |  |

* = 10% SIG
+ = 5% SIG
# = 1% SIG

Deposits Applicants have made a deposit of at least 2500 seeds of Inbred Sunflower Line C9607CM with The American Type Culture Collection (ATCC), Mansassas, VA 20110 USA, ATCC Deposit No. PTA-2423. The seeds deposited with the ATCC on Aug. 28, 2000 were taken from the pilot maintained by Pioneer Hi-Bred International, Inc., 800 Capital Square, 400 Locust Street, Des Moines, Ia. 50309-2340 since prior to the filing date of this application. This deposit of the Inbred Sunflower Line C9607CM will be maintained in the ATCC depository, which is a public depository for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801–1.809, including providing an indication of the viability of the sample. Applicants impose no restrictions on availability of the deposited material from the ATCC; however, Applicants have no authority to waive any restrictions imposed by law on the transfer of biological material or its transportation in commerce. Applicants do not waive any infringement of rights granted under this patent or under the Plant Variety Protection Act (7 USC 2321 et seq.). U.S. Plant Variety Protection of C9607CM has been applied for under application Ser. No. 9900332.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant inbred and the like may be practiced within the scope of the invention, as limited only by the scope of the appended claims.

What is claimed is:

1. Seed of sunflower inbred line designated C9607CM, representative samples having been deposited under ATCC Accession No. PTA-2423.

2. A sunflower plant, and parts thereof, having all the physiological and morphological characteristics of inbred line C9607CM, representative seed of said line having been deposited under ATCC accession No. PTA-2423.

3. The sunflower plant of claim 2, wherein said plant is male sterile.

4. A tissue culture of regenerable cells of a sunflower plant of inbred line C9607CM, wherein the tissue regenerates plants capable of expressing all the morphological and physiological characteristics of the inbred line C9607CM, representative seed of which have been deposited under ATCC Accession No. PTA-2423.

5. A tissue culture according to claim 4, the cells or protoplasts being of a tissue selected from the group consisting of leaves, pollen, embryos, roots, root tips, anthers, flowers and stalks.

6. A sunflower plant regenerated from the tissue culture of claim 4, capable of expressing all the morphological and physiological characteristics of inbred line C9607CM, representative seed of which have been deposited under ATCC Accession No. PTA-2423.

7. A method for producing a first generation ($F_1$) hybrid sunflower seed comprising crossing the plant of claim 2 with a different inbred parent sunflower plant and harvesting the resultant first generation ($F_1$) hybrid sunflower seed.

8. The method of claim 7 wherein inbred sunflower plant of claim 2 is the female or male parent.

9. An $F_1$ hybrid seed produced by crossing the inbred sunflower plant according to claim 2 with another, different sunflower plant.

10. An $F_1$ hybrid plant, and parts thereof, grown from the seed of claim 9.

11. The process for producing inbred C9607CM representative seed of which having been deposited under ATCC Accession No. PTA-2423 comprising:

a) planting a collection of seed comprising seed of a hybrid, one of whose parents is inbred C9607CM, said collection also comprising seed of said inbred;

b) growing plants from said collection of seed;

c) identifying said inbred C9607CM plant;

d) selecting said inbred C9607CM plant; and e) controlling pollination in a manner which preserves the homozygosity of said inbred C9607CM plant.

12. The process of claim 11 wherein step c) comprises identifying plants with decreased vigor.

13. The process of claim 11 wherein step c) comprises identifying seeds or plants with homozygous genotype.

14. A method for producing a C9607CM-derived sunflower plant comprising:

a) crossing inbred sunflower line C9607CM with a second sunflower plant to yield progeny sunflower seed;

b) growing said progeny sunflower seed, under plant growth conditions, to yield said C9607CM-derived sunflower plant.

15. A C9607CM-derived sunflower plant or parts thereof, produced by the method of claim 14, said C9607CM-derived sunflower plant expressing a combination of at least two C9607CM-derived traits selected from the group consisting of: a non oilseed type sunflower, high yielding, possesses genes capable of restoring fertility to hybrids possessing PET 1 cytoplasm, tall plant stature, large seeds, an average flowering time of 63 days from planting, an average of 103 days to harvest ripeness, basal branching with above average number of long cordate leaves, very good general appearance, and long seeds with broad black and narrow white striping.

16. The method of claim 14 further comprising:

c) crossing said C9607CM-derived sunflower plant with itself or another sunflower plant to yield additional C9607CM-derived progeny sunflower seed;

d) growing said progeny sunflower seed of step c) under plant growth conditions, to yield additional C9607CM-derived sunflower plants;

e) repeating the crossing and growing steps of c) and d) from 0 to 5 times to generate further C9607CM-derived sunflower plants.

17. A C9607CM-derived sunflower plant or parts thereof, produced by the method of claim 16, said C9607CM-derived sunflower plant expressing a combination of at least two C9607CM-derived traits selected from the group consisting of: a non oilseed type sunflower, high yielding, possesses genes capable of restoring fertility to hybrids possessing PET 1 cytoplasm, tall plant stature, large seeds, an average flowering time of 63 days from planting, an average of 103 days to harvest ripeness, basal branching with an above average number of long cordate leaves, very good general appearance, and long seeds with broad black and narrow white striping.

18. The method of claim 14 still further comprising utilizing plant tissue culture methods to derive progeny of said C9607CM-derived sunflower plant.

19. A C9607CM-derived sunflower plant or parts thereof produced by the method of claim 18, said C9607CM-derived sunflower plant expressing a combination of at least two C9607CM-derived traits selected from the group consisting of: a non oilseed type sunflower, high yielding, possesses genes capable of restoring fertility to hybrids possessing PET 1 cytoplasm, tall plant stature, large seeds, an average flowering time of 63 days from planting, an average of 103 days to harvest ripeness, basal branching with an above average number of long cordate leaves, very good general appearance, and long seeds with broad black and narrow white striping.

20. The sunflower plant or parts thereof of claim 2 wherein the plant or parts thereof have been transformed so that its genetic material contains one or more transgenes operably linked to one or more regulatory elements.

21. A method for producing a sunflower plant that contains in its genetic material one or more transgenes, comprising crossing the sunflower plant of claim 20 with either a second plant of another sunflower line, or a non-transformed sunflower plant of the line C9607CM, so that the genetic material of the progeny that result from the cross contains the transgenes operably linked to a regulatory element.

22. A sunflower plant or parts thereof produced by the method of claim 21.

23. A sunflower plant or parts thereof wherein at least one ancestor of said sunflower is the sunflower plant of claim 2, said sunflower plant expressing a combination of at least two C9607CM-derived traits selected from the group consisting of: a non oilseed type sunflower, high yielding, possesses genes capable of restoring fertility to hybrids possessing PET 1 cytoplasm, tall plant stature, large seeds, an average flowering time of 63 days from planting, an average of 103 days to harvest ripeness, basal branching with an above average number of long cordate leaves, very good general appearance, and long seeds with broad black and narrow white striping.

24. A method for developing a sunflower plant in a sunflower plant breeding program using plant breeding techniques, which include employing a sunflower plant or its parts as a source of plant breeding material comprising: obtaining the sunflower plant or its parts of claim 2 as a source of said breeding material.

25. The sunflower plant breeding program of claim 24 wherein plant breeding techniques are selected from the group consisting of: recurrent selection, backcrossing, pedigree breeding, restriction fragment length polymorphism enhanced selection, genetic marker enhanced selection, and transformation.

26. A sunflower plant or parts thereof produced by the method of claim 24.

\* \* \* \* \*